(12) United States Patent
Tan et al.

(10) Patent No.: US 8,471,035 B1
(45) Date of Patent: Jun. 25, 2013

(54) TWO-PHOTON ABSORBING ARYLAMINE-ENDCAPPED AND DIALKYLFLUORENE-BRIDGED BENZOBISTHIAZOLE COMPOUNDS WITH HIGH OLEOPHILICITY

(75) Inventors: Loon-Seng Tan, Centerville, OH (US); Ramamurthi Kannan, Cincinnati, OH (US); Matthew Dalton, Bellbrook, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 13/475,159

(22) Filed: May 18, 2012

Related U.S. Application Data

(60) Provisional application No. 61/487,774, filed on May 19, 2011.

(51) Int. Cl.
*C07D 513/04* (2006.01)

(52) U.S. Cl.
USPC .......................................................... 548/151

(58) Field of Classification Search
USPC .......................................................... 548/151
See application file for complete search history.

(56) References Cited

U.S. PATENT DOCUMENTS

| | | | |
|---|---|---|---|
| 5,521,277 A | 5/1996 | Tan et al. |
| 5,534,613 A | 7/1996 | Tan et al. |
| 5,633,337 A | 5/1997 | Tan et al. |
| 6,696,142 B2 | 2/2004 | Baer et al. |
| 6,730,793 B1 | 5/2004 | Kannan et al. |
| 2007/0052350 A1 | 3/2007 | Su et al. |
| 2010/0102761 A1 | 4/2010 | Von Malm et al. |
| 2011/0108813 A1 | 5/2011 | Kohiro et al. |

OTHER PUBLICATIONS

Reaxysfile on STN CAS Online, Accession No. 11872719, entry date Jun. 18, 2008.*
He, Guang S.; Tan, Loon-Seng; Zheng, Qingdong; Prasad, Paras N., "Multiphoton Absorbing Materials: Molecular Designs, Characterizations, and Applications", Chemical Reviews (2008), 108(4), 1245-1330.
Kevin D. Belfield, Sheng Yao, Alma R. Morales, Joel M. Hales, David J. Hagan, Eric W. Van Stryland, Victor M. Chapela, Judith Percino, "Synthesis and characterization of novel rigid two-photon absorbing polymers", Polymers for Advanced Technology (2005) 16: 150-155.
Tan, Loon-Seng; Srinivasan, K. R.; Bai, Shih Jung; Spry, Robert J., "New aromatic benzazole polymers II: synthesis and conductivity of benzobisthiazole-co-polymers incorporated with 4-N,N-dimethylaminotriphenylamine groups", Journal of Polymer Science, Part A: Polymer Chemistry (1998), 36(5), 713-724.
Jenekhe, Samson A.; Osaheni, John A.; Meth, Jeffrey S.; Vanherzeele, Herman, "Nonlinear optical properties of poly(p-phenylenebenzobisoxazole", Chemistry of Materials, (1992) vol. 4, Issue 3, pp. 683-687.
Tan, Loon-Seng; Srinivasan, K. R.; Bai, Shih Jung, "New aromatic benzazole polymers I: Benzobisthiazole and benzobisoxazole polymers with main-chain triarylamino units", Journal of Polymer Science, Part A: Polymer Chemistry (1997), 35(10), 1909-1924.
Loon-Seng Tan, Matthew J Dalton, Rachel Jakubiak, Ramamurthi Kannan, Nikolay Makarov, Aleks Rebane, Augustine M Urbas, Thomas M Cooper, "Synthesis and Characterization of a Novel Film-Forming, Two-Photon Absorbing Benzobisthiazole Polymer and Related Model Compound", Abstract for poster presentation at "9th International Symposium on Functional Pi-Electron Systems" Conference, Georgia Institute of Technology, Atlanta, GA, May 23-28, 2010.

* cited by examiner

*Primary Examiner* — Laura L. Stockton
(74) *Attorney, Agent, or Firm* — AFMCLO/JAZ; Bart Hersko

(57) ABSTRACT

Two-photon absorbing arylamine-endcapped and dialkylfluorene-bridged benzobisthiazole-based compounds are provided. These two-photon absorbing benzobisthiazole-based compounds show high solubility in nonpolar hydrocarbon solvents (oleophilicity) and high two-photon properties, especially in the nanosecond domain of pulse-laser excitation.

11 Claims, No Drawings

TWO-PHOTON ABSORBING ARYLAMINE-ENDCAPPED AND DIALKYLFLUORENE-BRIDGED BENZOBISTHIAZOLE COMPOUNDS WITH HIGH OLEOPHILICITY

CROSS REFERENCE TO RELATED APPLICATION

This application claims the benefit of and priority to the filing date of U.S. provisional application Ser. No. 61/487,774 filed May 19, 2011, incorporated herein by reference in its entirety.

RIGHTS OF THE GOVERNMENT

The invention described herein may be manufactured and used by or for the Government of the United States for all governmental purposes without the payment of any royalty.

BACKGROUND OF THE INVENTION

The present invention relates to two-photon absorbing, benzobisthiazole-based chromophores with high oleophilicity as indicated by their high solubility in hydrocarbon solvents.

Multiphoton absorption (MPA) is a nonlinear optical process that occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (2PA), two quanta of photons may be absorbed from a single light source (degenerate 2PA) or two sources of different wavelengths (non-degenerate 2PA). In considering the practical exploitation of 2PA process, it is important to recognize the following useful features of the 2PA phenomenon, based on the fact that 2PA scales nonlinearly with the squared intensity of the incident laser beam: (i) upconverted emission, whereby an incident light at lower frequency (energy) can be converted to an output light at higher frequency, for instance, near infrared (NIR) to ultraviolet (UV) upconversion; (ii) deeper penetration of incident NIR light than UV light that may be hazardous with prolonged exposure; (iii) highly localized excitation as compared with one-photon processes allowing for precise spatial control of in situ photochemical or photophysical events in the absorbing medium, thereby minimizing undesirable activities such as photodegradation or photobleaching; and (iv) fluorescence (i.e. light emission via relaxation from singlet excited state to ground state) when properly manipulated, that would allow for information/signal feedback or amplification in conjunction with other possible, built-in effects such as surface plasmonic enhancement effect. It is anticipated that further ingenious utilization of these basic characteristics will lead to practical applications other than those already emerged in such diverse areas as bio-medical fluorescence imaging, data storage, directed energy protection, hazardous chemical detection, microfabrication of microelectromechanical systems (MEMS), photodynamic therapy, etc. In the past two decades, significant advances have been made in the fundamental understanding of structure-property relationship that has led to the design and synthesis of two-photon absorbers with very large cross-section values. Although further enhancement of 2PA cross-section is still possible as suggested by a number of theoretical studies, for certain applications, the two-photon-property requirement has essentially been met by the state-of-art chromophores. Because of the possible structure-property-processing trade-off, which requires certain balancing, the secondary properties, i.e. thermal and mechanical properties as well as practical solubility in aqueous and/or common organic solvents, are especially important to material processing into various useful forms (films, coatings, fibers, windows etc.) and device configurations.

In the inventors' previous work as documented in U.S. Pat. No. 6,730,793, Ramamurthi Kannan et al, issued May 4, 2004, a suite of quadrupolar and octupolar two-photon absorbing compounds based on the "Donor-Acceptor-Donor" structural motif were claimed. Among these 2PA compounds were quadrupolar examples based on diphenylamine-benzobisthiazole-diphenylamine motif, which have the attractive properties of high two-photon absorptivity and easily accessible starting material for the construction of the benzobisthiazole structure as the electron-accepting core.

Accordingly, it is an object of the present invention to provide a new series of highly hydrocarbon-soluble, two-photon absorbing compounds with a common 2,6-benzobisthiazolyl core with both sides connected to 9,9-dialkylfluorenyl moieties, and endcapped with extended arylamino groups. They have been synthesized via a Suzuki cross-coupling reaction of a new benzobisthiazole-containing dibromide precursor and a triphenylamine(boronate ester) and amination of the same bromo precursor with diphenylamine. These conjugated aromatic-heterocyclic compounds show high solubility in nonpolar hydrocarbon solvents (oleophilicity) and high two-photon properties, especially in the nanosecond domain of pulse-laser excitation.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention, there are provided new 2PA chromophores of the formula:

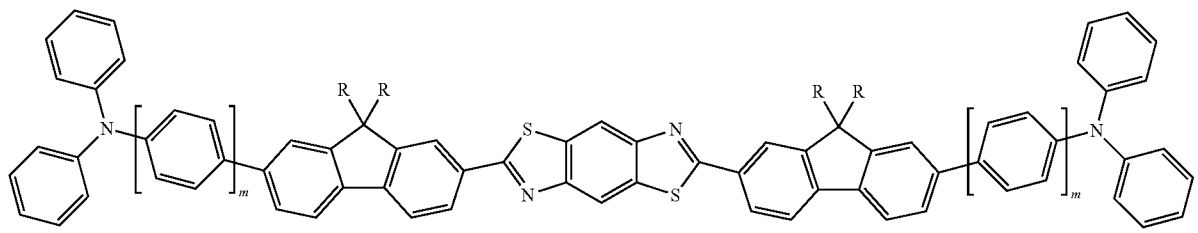

where m=0, 1, or 2; R is an alkyl chains, $C_nH_{2n+1}$, where n=10-20. Preferably, m=1 and R are branched alkyl chains such as 3,7-dimethyloctyl ($C_{10}H_{21}$), 3,7,11-trimethyldodecyl ($C_{15}H_{31}$), and 3,7,11,15-tetramethylhexadecyl ($C_{20}H_{41}$).

DETAILED DESCRIPTION

The general synthetic scheme of the benzobisthiazole-based AFX chromophores is depicted in Scheme 1. Compound 1 is synthesized from the one-pot, double alkylation of commercially available 2,7-dibromofluorene with an appropriate branched alkyl bromide in alkaline aqueous DMSO or THF solution. By monolithiating compound 1, followed by addition of N,N-dimethylformamide (DMF) as a formylating agent, bromo-dialkylfluorene-carboxaldehyde (2) is obtained. The dibromo-benzobisthiazole intermediate (3) is then prepared via a double oxidative condensation of two equivalents of bromo-dialkylfluorene-carboxaldehyde (2) and 2,5-diaminobenzene-1,4-dithiol (DABDT).

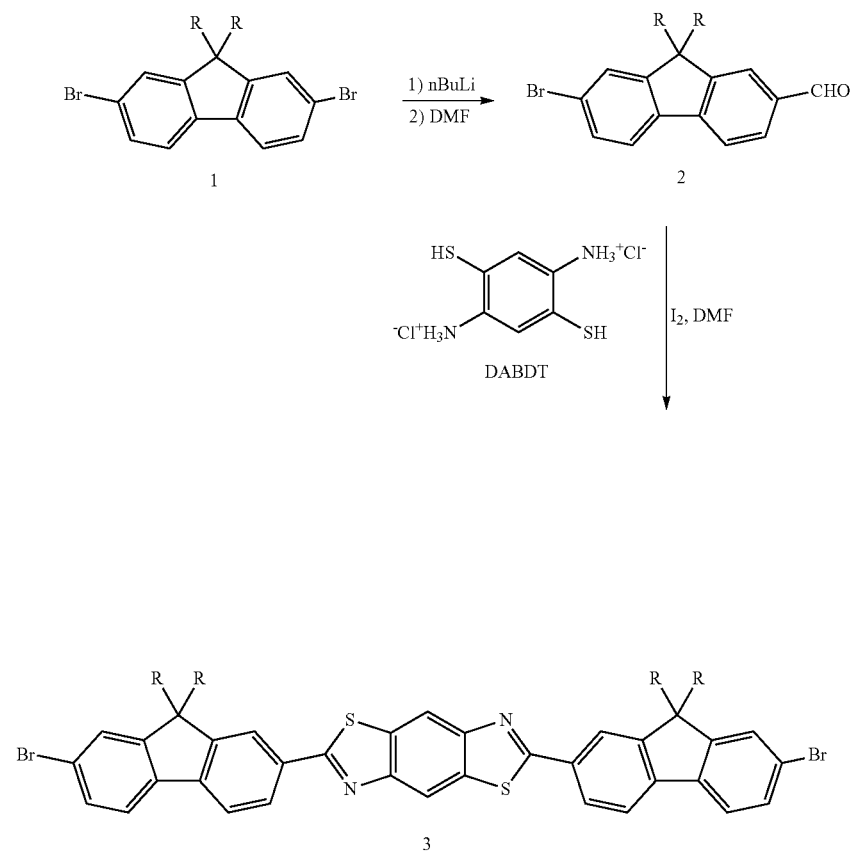

-continued
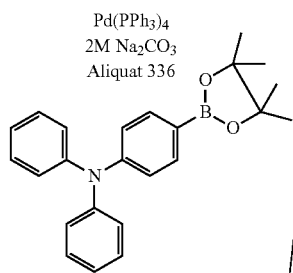
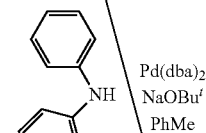
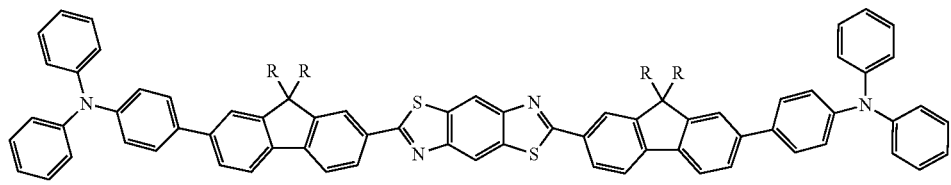
4
AF-388-XXX
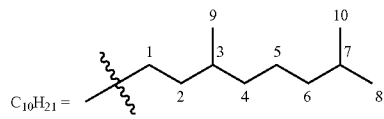
5
AF-358-XXX
R =
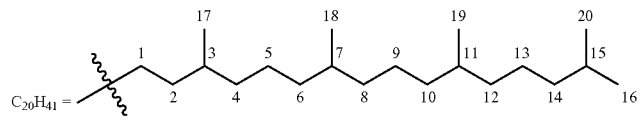
(3,7-dimethyloctyl)
(XXX = 118)
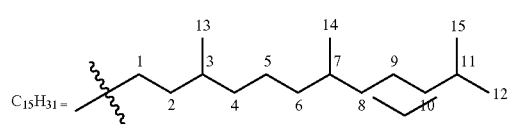
(3,7,11,15-tetramethylhexadecyl)
(XXX = 312)
(3,7,11-trimethyldodecyl)
(XXX = 416)

Scheme 1: A General Synthetic Scheme for Benzobisthiazole-Based AFX Chromophores Compound 3 and its derivatives with endgroups such as trialkylstannyl or fluorinated alkylsulfonate (e.g. trifluoromethanesulfonate or commonly known as triflate), instead of dibromo endgroups, are useful as monomers in palladium-catalyzed polymerization reactions. It is noted that there are multiple purposes of having the branched alkyl side-chains (R group that is 3,7-dimethyloctyl and higher homologs) in compound 4 [designated generically as AF388-XXX, where -XXX is the R group defined by a particular branched alkyl chain. For example, AF388-118 is compound 4 with R=3,7-dimethyloctyl group, i.e. two methyl groups at different (1,1) locations on an octyl (C-8) backbone; see Scheme 1], namely to promote (i) solubility during polymerization, (ii) ease in film fabrication and (iii) frustrating the aggregation of the benzobisthiazole-fused structure in solid-state (cast film). The subject two-photon chromophores (i.e. compound 4 & 5; compound 5 is designated generically as AF358-XXX) are obtained by endcapping compound 3, via a palladium-catalyzed cross-coupling reaction, with either diphenylamine or a monoboronate-functionalized triphenylamine, which is prepared from 4-bromotriphenylamine, via lithiation reaction with n-butyllithium, followed by borylation with isopropoxydioxaborolane.

In an alternative synthetic route (see Scheme 2) to compounds 4 and 5, the syntheses of AF-388-118 and AF-388-312 illustrate the viability. This alternative route has the same number of synthetic steps and provides comparable overall yields, but it has the advantage of requiring fewer needs in column-chromatographic purification because the intermediates, which are without the long and branched alkyl chains, are sufficiently crystalline to allow purification via simple recrystallization. Thus, compound 7, i.e. the non-alkylated analog of compound 3, is prepared from a double oxidative condensation of 2,5-diamino-benzene-1,4-dithiol with two equivalents of 2-bromofluorene-9-carboxaldehyde (compound 6). Tetraalkylation with appropriate branched bromoalkane in the presence of potassium t-butoxide in THF then generates compound 3. In this way, the synthesis of compound 3 is delayed to the late stage of the synthetic sequence to eliminate the need for labor-intensive, chromatographic-column purification of the precursor, 2-bromofluorene-9-carboxaldehyde (compound 6) as well as that for the intermediates in the original synthesis (Scheme 1). Compound 6 could be prepared from a "formylation" reaction of commercially available 2-bromofluorene through the agency of dichloromethylmethyl ether via tandem Friedel-Crafts alkylation and oxo-dichloro exchange reaction.

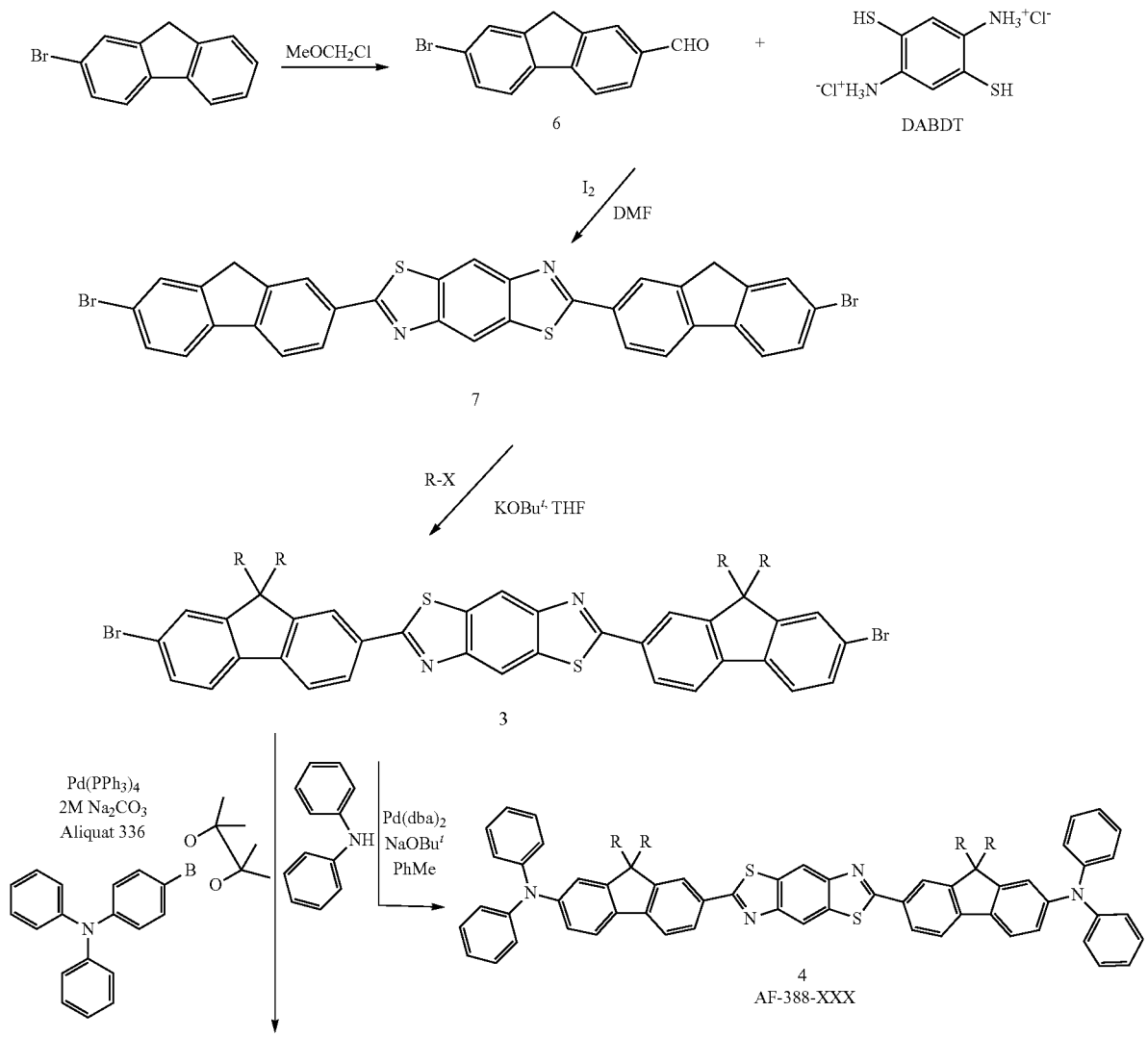

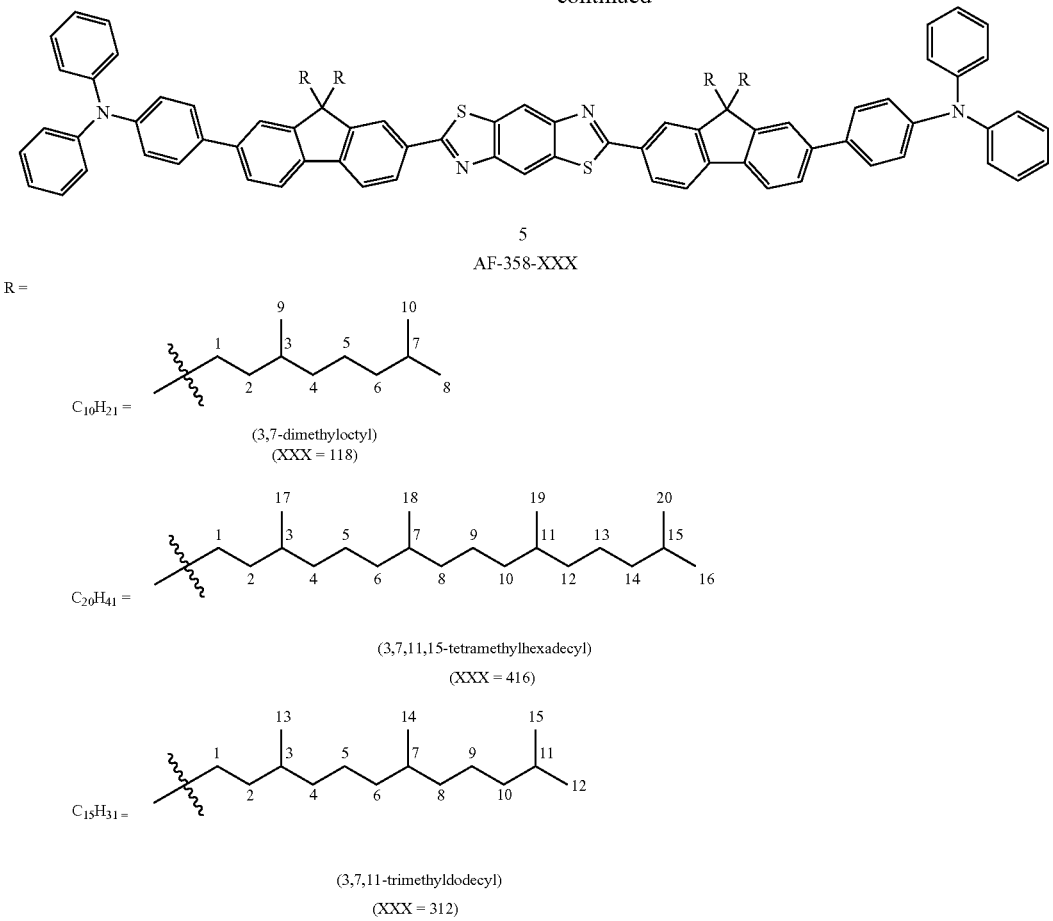

5
AF-358-XXX

Scheme 2: Alternate Synthetic Route to Benzobisthiazole-Based AFX Chromophores

Unlike analogous rod-shaped benzobisthiazole-compounds which precipitate out of hydrocarbon solutions upon standing at room temperature, the subject benzobisthiazole compounds with long and multi-branched alkyl chains are exceedingly soluble in hydrocarbon solvents such as hexane and toluene. For example, it was found that ≧30 wt % of AF-388-312 molecules (with 3-branched C-15 alkyl chains, i.e. 3,7,11-dimethyldodecyl groups) and ≧51 wt % of AF-388-416 molecules (with 4-branched C-20 alkyl chains, i.e. 3,7,11,15-trimethyldodecyl groups) remained completely dissolved in hexane for months under ambient conditions.

The chromophores of this invention can be synthesized following the procedures given in the following examples, which illustrate the invention:

EXAMPLE 1

Racemic 1-Bromo-3,7-dimethyloctane (Dihydrocitronellyl Bromide)

Concentrated sulfuric acid (17 mL) was added to 48% hydrobromic acid (100 mL) with stirring, and then 3,7-dimethyloctanol (dihydrocitronellol, Aldrich, 67 mL, 100 g) was added to the mixture. The mixture was then heated to 120-125° C., and kept at this temperature for 3 hours. The reaction was cooled, and extracted into heptane (300 mL). The heptane layer was washed with hydrochloric acid, water, sodium bicarbonate solution, dried and concentrated to leave an oil, 81.5 g. This oil was distilled under vacuum at a bath temperature of 120-125° C., to afford the bromide product as an oil, b.p. 85-87° C./10 mmHg, 78.2 g, 100% yield. Mass Spec: m/z 220, 222 (M+).

EXAMPLE 2

3,7,11-Trimethyldodecanol (Hexahydrofarnesol)

Hydrogenation Using Platinum on Charcoal:

A mixture of farnesol (3,7,11-trimethyl-2,6,10-dodecatrien-1-ol) (38.96 g), ethanol (135 mL), and platinum on carbon catalyst (5%, 0.97 g) was hydrogenated in a Parr hydrogenator at an initial pressure of 59 psi at room temperature for 7 hours, refilling the reactor with hydrogen when necessary. The fall in pressure was 35 psi, and the rate of consumption was less than 1 psi an hour. To the mixture acetic acid (10 mL) and additional catalyst (0.55 g) were added and the hydrogenation was continued at an initial pressure of 62 psi for 24 hours when another 13 psi of hydrogen was consumed. The total hydrogen consumption of 48 psi is less than the theoretical 53 psi. The mixture was filtered, and the filtrate was concentrated. The residue was extracted into toluene, and the toluene extract was washed with water, dried and concentrated. The crude product was distilled under vacuum. Fraction by 80-82° C./0.5 mm, 6.08 g (16% yield) was 3,7,11-trimethyl dodecanol. Mass spec: m/z 212 (M+). Later fraction, by 114-119° C., 30.09 g (75% yield) was the desired product. Mass spec: m/z 226 (M−2). Anal. Calcd. for $C_{15}H_{32}O$: C, 78.87%; H, 14.12%. Found: C, 78.87%; H, 13.62%.

(b) Hydrogenation Using Raney Nickel:

Under nitrogen in a 1 liter 3-neck flask equipped with mechanical stirring, Raney Nickel (Raney 2800, Aldrich, 30% slurry in water, 20.4 g) was suspended in ethanol (400 mL). A solution of farnesol (mixture of cis and trans isomers, 25.0 g), in ethanol (75 mL) was added dropwise with a gentle sweep of hydrogen through the reaction mixture, and the mixture was stirred under hydrogen for 144 hours. Hydrogen was then replaced by nitrogen, and under a positive pressure of nitrogen the suspension was filtered through a filter stick. The catalyst was suspended in a small volume of ethanol and the filtration was repeated. Finally the catalyst was suspended in water and the suspension was rejected. The ethanol filtrate was filtered again through celite and the filtrate was concentrated. After extractive work-up using toluene, the residue was distilled under vacuum. The desired product, by 112-115° C., was obtained as a colorless liquid, 22.76 g (88% yield). Mass spec: m/z 226 (M−2)$^+$. Anal. Calcd for $C_{15}H_{32}O$: C, 78.88%; H, 14.12%. Found: C, 77.90%; H, 14.32%. No hydrocarbon was detected in the fore-run (0.28 g) or distillation residue (0.9 g). The alcohol product was converted to the corresponding bromide, without additional purification.

EXAMPLE 3

3,7,11-Trimethyldodecyl Bromide
(Hexahydrofarnesyl Bromide)

Method A:

3,7,11-Trimethyldodecanol (Example 2) (22.22 g, 0.1 mole) was reacted with 48% hydrobromic acid (22.5 mL, 0.22 mole) and concentrated sulfuric acid (12.0 mL) in a manner similar to the preparation of dihydrocitronellyl bromide (see Example 1). The product was purified by column chromatography, 24.43 g (84% yield). Mass spec: m/z 290, 292 (M$^+$). Anal. Calcd for $C_{15}H_{31}Br$: C, 61.85%; H, 10.73%; Br, 27.43%. Found: C, 61.85%; H, 10.50%; Br, 27.86%. $^1$H NMR (CDCl$_3$), δ ppm: 0.84-0.90 (2 doublets, 12H), 1.05-1.67 (m, 17H), 3.38-3.46 (m, 2H). $^{13}$C NMR (CDCl$_3$) δ ppm: 19.08, 19.15, 19.81, 19.87, 22.78, 22.88, 24.37, 24.95, 24.96, 28.12, 31.77, 31.81, 32.29, 32.88, 32.90, 36.92, 36.98, 37.37, 37.40, 37.43, 37.50, 39.50, 40.18, and 40.25 (24 sp$^3$C).

Method B:

A mechanically stirred mixture of hexahydrofarnesol (Example 2; 87 g, 0.38 mol), triphenylphosphine (104.98 g, 0.40 mol) was cooled to 0° C. N-Bromosuccinimide (71.13 g, 0.4 mol) was added in portions over 45 minutes. The mixture was stirred for 18 hours at room temperature. Methylene chloride was rota-evaporated off on a rotavap and the residual solids were extracted with hexane. Then, the hexane extract was passed through a column of silica gel. Evaporation of hexane eluates left the bromide product as a colorless liquid, 105.05 g, (95% yield). Mass spec: m/z 290, 292 (M$^+$). Anal. Calc. for $C_{15}H_{31}Br$: C, 61.85%; H, 10.73%; Br, 27.43%. Found: C, 60.77%; H, 9.89%; Br, 27.58%.

EXAMPLE 4

3 7,11,15-tetramethyl-hexadecanol (Dihydrophytol)

Method A, Hydrogenation Over Platinum:

A mixture of ethanol (230 mL), 3,7,11,15-tetramethyl-2-hexadecen-1-ol (phytol, mixture of cis and trans isomers, 51.38 g), and platinum on carbon (5%, 1.46 g) was hydrogenated at room temperature at an initial pressure of 58 psi for 3 hours when the pressure reduction was 17 psi (theory-17 psi). The crude product, 51.76 g, obtained after initial work-up involving filtration and extraction into toluene, was distilled. The desired product, 27.22 g (53% yield) had by 144-146° C./0.2 mm. Mass spec: m/z 298 (M$^+$). Anal. Calcd for $C_{20}H_{42}O$: C, 80.46%; H, 14.18%. Found: C, 79.51%; H, 13.69%. Earlier fractions with combined weight of 22.42 g were a mixture of the desired product and product of hydrogenolysis (m/z 282). It is estimated that the saturated hydrocarbon was formed in 17% yield.

Method B, Hydrogenation Over Nickel:

Phytol (200.45 g) was hydrogenated at room temperature in ethanol (1 lit) with 30% slurry of Raney Nickel (85.7 g), with a stream of hydrogen for 104 hours to get dihydrophytol, 201.87 g (100%). Mass spec: m/z 297 (M−1)$^+$. $^1$H NMR (CDCl$_3$), δ ppm: 0.83-0.88 (m, 15H), 1.04-1.53 (m, 24H), 1.75 (s), 3.60-3.71 (m 2H). This product is used without further purification in the conversion to the corresponding bromide.

EXAMPLE 5

3,7,11,15-Tetramethylhexadecyl Bromide
(Dihydrophytyl Bromide)

Method A. with HBr Solution:

To a mixture of dihydrophytol (Example 4) (27.0 g), and 48% hydrobromic acid (270 mL), concentrated sulfuric acid (27.0 mL) was added dropwise, and then was held at reflux (125-127° C.) for 5 hours. The dark gel that resulted on cooling was extracted with ether, and the ether extract was washed with water, bicarbonate solution and dried. The residue left on removal of ether was chromatographed over silica gel. Elution with heptane gave the desired bromide as a colorless liquid, 28.47 g (87% yield). Mass spec: m/z 360, 362 (M$^+$). Anal. Calcd for $C_{20}H_{41}Br$: C, 66.46%; H, 11.43%; Br, 22.11%. Found: C, 66.39%; H, 11.99%; Br, 22.26%.

Method B, with NBS and Triphenyl Phosphine:

A solution of dihydrophytol (Example 4; 42.5 g, 0.143 mol), and triphenyl phosphine (41.14 g, 0.157 mol), in methylene chloride (125 mL) was cooled to 0° C. and N-bromosuccinimide (26.15 g, 0.157 mol) was added in portions keeping the temperature below 10° C. After 18 hours at room temperature, methanol (5 mL) was added and the mixture was allowed to concentrate. The residue was suspended in hexanes and the hexane solution was passed through a column of silica gel and then evaporated to dryness. The product, 49.83 g (97% yield) was obtained as a colorless liquid. Mass spec: m/z 360, 362 (M$^+$). Anal. Calcd for $C_{20}H_{41}Br$: C, 66.46%; H, 11.43%; Br, 22.11%. Found: C, 66.86%; H, 11.28%; Br, 22.21%. $^1$H NMR (CDCl$_3$), δ ppm: 0.85-0.90 (m, 15H), 1.06-1.66 (m, 24H), 3.37-3.47 (m, 2H).

EXAMPLE 6

Racemeic and Meso-2,7-dibromo-9,9-bis(3,7-dimethyloctyl)fluorene

To a mechanically stirred mixture of 2,7-dibromofluorene (58.32 g, 0.18 mol), potassium iodide (3.0 g, 18 mmol), potassium hydroxide (50.4 g, 0.9 mol) and DMSO (150 mL), cooled in ice-water to 15° C., dihydrocitronellyl bromide (Example 1; 86.8 g, 0.392 mol) was added, and the mixture was stirred at room temperature for 18 hours. The mixture was poured into water, and the product was extracted into a mixture of 1:1 toluene-heptane. The organic phase was washed with water, dried and concentrated. The residual oil was refluxed with pyridine for 18 hours to quarternize any unreacted dihydrocitronellyl bromide, and the mixture was diluted with toluene-heptane, and the organic phase was washed with water, dried and concentrated. The residual orange oil was transferred to a column of 1050 g of alumina. Elution with hexanes (1800 mL) gave the product, 102.25 g, 94% yield, as a colorless oil. Mass Spec: m/z 602, 604, 606 (M$^+$). Anal. Calcd. for $C_{33}H_{48}Br_2$: C, 65.56%; H, 8.00%; Br, 26.44%. Found: C, 65.80%; H, 7.81%; Br, 26.30%.

EXAMPLE 7

2,7-Dibromo-9,9-bis(3,7,11-trimethyldodecyl)fluorene

To a flask containing a solution of 2,7-dibromofluorene (50.0 g, 0.154 mol) in freshly distilled THF (500 mL) was added potassium tert-butoxide (36.4 g, 0.324 mol), and the solution quickly turned red. After stirring for 30 min, a solution of 1-bromo-3,7,11-trimethyldodecane (97.7 g, 0.335 mol) in THF (75 mL) was added dropwise over 3 hr, and the mixture was allowed to stir overnight. Water (400 mL) was added, followed by 500 mL of toluene, and the organic phase was washed with water and brine, dried with $MgSO_4$, filtered, and concentrated in vacuo. The residual orange-red oil was purified in portions by column chromatography eluting with hexanes to give a colorless oil (109 g, 95% yield). $^1$H NMR (400 MHz, $CDCl_3$) δ 7.52 (d, J=8 Hz, 2H), 7.41-7.46 (m, 4H), 1.83-2.0 (m, 4H), 1.51 (sept, 2H, J=6.6 Hz), 0.91-1.35, (br. m, 28H), 0.86 (d, J=6.6 Hz, 12H), 0.78 (dd, $J_1$=1.5 Hz, $J_2$=6.5 Hz, 6H), 0.69 (d, J=6.5 Hz, 6H), 0.5-0.6 (m, 2H), 0.36-0.5 (m, 2H); $^{13}$C NMR (100 MHz, $CDCl_3$) δ 152.48, 139.13, 130.14, 126.10, 121.46, 121.10, 55.50, 39.35, 37.42, 37.33, 37.24, 36.62, 36.60, 32.79, 32.75, 32.71, 32.28, 30.39, 30.26, 27.97, 24.80, 24.77, 24.24, 22.73, 22.63, 19.70, 19.61; MS (m/z): 742, 744, 746 (M$^+$); Anal. Calcd. for $C_{43}H_{68}Br_2$: C, 69.34%; H, 9.20%; Br, 21.45%. Found: C, 69.51%; H, 9.30%; Br, 21.29%.

EXAMPLE 8

2,7-Dibromo-9,9-bis(3,7,11,15-tetramethylhexadecyl)fluorene (2,7-Dibromo-9,9-bis(dihydrophytyl) fluorene)

After a mixture of 2,7-dibromofluorene (9.75 g, 0.03 M) dissolved in THF (200 mL anhy.) and potassium tert-butoxide (10.12 g, 0.09 M) had been stirred for half an hour under argon, 3,7,11,15-tetramethylhexadecyl bromide (Example 5) was added dropwise into the reaction flask via an addition funnel over a period of 20 minutes. The resulting deep red solution was stirred for an additional 24 hrs. Then, toluene (100 mL) was added, followed by water (100 mL). The organic layer was separated and washed with brine, and the aqueous layers were further extracted with toluene. The combined organic layers were then dried filtered and concentrated in vacuo. Flash chromatography of the crude product on silica with hexanes yielded a colorless oil as the desired product. Yield: 22.8 g (86%) Anal. Calcd. for $C_{53}H_{88}Br_2$: C, 71.92%; H, 10.02%; Br, 18.05%. Found C, 72.35%; H, 10.13%; Br, 17.96%. $^1$H NMR (400 MHz, $CDCl_3$), δ: 7.5 (d, 2H), 7.45 (m, 4H), 1.9 (m), 1.5 (m), 1.4-1.0 (m broad), 0.88-0.83 (m), 0.79 (d, 6H); 0.69 (d, 6H) $^{13}$C NMR (400 MHz, $CDCl_3$), δ: 152.45, 139.11, 130.14, 126.08, 121.48, 121.09, 55.48, 39.37, 37.45, 37.40, 37.29, 37.24, 36.61, 36.59, 32.78, 32.76, 30.37, 30.23, 27.99, 24.83, 24.50, 24.47, 24.25, 22.77, 22.67, 19.79, 19.76, 19.72, 19.70, 19.67, 19.60, 19.49, 19.42. Mass Spec: m/z 884.73 (M$^+$).

EXAMPLE 9

7-Bromo-9,9-bis(3,7-dimethyloctyl)-fluorene-2-carbaldehyde

To a flame-dried 3-neck round-bottomed flask equipped with a mechanical stirrer and an addition funnel was added 2,7-dibromo-9,9-bis(3,7-dimethyloctyl)fluorene (Example 6; 79.3 g, 131.2 mmol) and THF (350 mL) by cannula. The solution was cooled to −78° C. and 2.5 M n-BuLi in hexane (52.5 mL, 131.2 mmol) was added by addition funnel over 15 min. After stirring for 30 min, N,N-dimethylformamide (DMF, 20.0 mL, 262 mmol) in THF (30 mL) was added dropwise, and the reaction mixture was allowed to warm to room temperature overnight. Toluene and water were added, and the organic phase was further washed with water, dried with $MgSO_4$, and concentrated. The crude product was purified by column chromatography eluting with heptane to 20% toluene/heptane to give 54 g (75%). $^1$H NMR (400 MHz, $CDCl_3$) δ: 10.06 (s, 1H), 7.88-7.79 (m, 3H), 7.63 (m, 1H), 7.51 (m, 2H), 1.41 (m, 2H), 1.20-0.93 (m, 12H), 0.92-0.75 (m, 14H), 0.66 (m, 6H), 0.60-0.30 (m, 4H). Mass Spec. m/z 552, 554 (M$^+$). Anal. Calcd. for $C_{34}H_{49}BrO$: C, 73.76%; H, 8.92%; Br, 14.43%. Found: C, 73.80%; H, 8.86%; Br, 14.64%.

EXAMPLE 10

2,6-Bis[7-bromo-9,9-bis(3,7-dimethyloctyl)fluoren-2-yl]-benzo[1,2-d;4,5-d']bisthiazole To a mixture of 7-bromo-9,9-bis(3,7-dimethyloctyl)fluorene-2-carbaldehyde (Example 9; 10.61 g, 19.2 mmol), 2,5-diaminobenzene-1,4-dithiol dihydrochloride (2.33 g, 9.6 mmol), tri-n-butylamine (5 mL, 21 mmol), and DMF (50 mL), at 40° C., iodine (2.5 g, 9.85 mmol) was added and the mixture was held at 107° C. for 5 hours. After cooling, tri-n-butylamine (5 mL, 21 mmol) was added, and the slurry was filtered. The resulting greenish-yellow solids were washed with methanol. The crude product was transferred to a column of alumina, and the column was eluted with a mixture of toluene and heptane (1:3) to get the product. Crystallization from heptane gave 7.2 g (61% Yield), m.p. 163-166° C. Mass spec: m/z 1236, and 1238, 1240 (M$^+$). Anal. Calcd for $C_{74}H_{98}N_2S_2Br_2$: C, 71.70%; H, 7.97%; N, 2.26%; S, 5.17%; Br, 12.89%. Found: C, 71.75%; H, 8.10%; N, 2.29%; S, 5.12%; Br, 13.13%. $^1$H NMR ($CDCl_3$), δ ppm: 0.42-0.56 (m, 4H), 0.57-0.67 (m, 4H), 0.68-0.73 (2d overlapping, 12H), 0.74-0.8 (m, 24H), 0.83-0.93 (m 4H), 0.95 1.21 (m 24H), 1.26-1.48 (m, 4H), 1.96-2.18 (m, 8H), 7.49-7.51 (m, 4H), 7.62 (d, 2H), 7.78 (d, 2H), 8.1 (s, 4H), and 8.57 (s, 2H). $^{13}$C NMR ($CDCl_3$), δ ppm: 19.44, 19.51, 22.52, 22.55, 22.64, 24.52, 24.55, 27.88, 27.91, 30.37, 30.43, 32.77, 36.48, 36.54, 37.47, 39.14, 55.59 (17 sp$^3$C), 115.12, 120.30, 121.68, 122.22, 126.25, 127.22, 130.27, 132.60, 134.43, 139.15, 143.38, 151.22, 152.27, 153.58, and 169.27 (15 sp$^2$C).

EXAMPLE 11

7-Bromo-fluorene-2-carbaldehyde

To a mechanically stirred solution of commercially available 2-bromofluorene (79.1 g 90% pure, 71.19 g at 100% purity, 0.29 mol) in 350 mL dichloromethane, in a 1-liter 3-neck round-bottomed flask, cooled in a ice-salt bath, tin (IV)chloride (60 mL, 133.56 g, 0.513 mol) was added. Maintaining the temperature at −2° C., over a period of 20 minutes, dichloromethyl methyl ether (33 mL, 41.94 g, 0.365 mol) was added dropwise, stirred near 0 to −1° C. for 1.5 hours, and then allowed to warm to room temperature over a period of 3 hours. The mixture was poured into crushed ice, and methylene chloride was allowed to evaporate. The product slurry was then filtered and washed with water. The dry crude product (mixture of two aldehydes) weighed 87.9 g, m.p. 138-144° C. This was stirred with 750 mL of 10% toluene-heptane at reflux for 2 hours, cooled and filtered at room temperature, 73.5 g, m.p. 161-170° C. This was dissolved in 400 mL hot toluene (hazy solution; tin salts might be still present) diluted with 300 mL heptanes, and the slurry was kept at reflux for 3 hours, cooled and collected at room temperature, 59.0 g, m.p. 176-179° C. A recrystallization by dissolution in toluene (600 mL), clarification while hot, and dilution with heptanes (300 mL) delivered 50 g of pure 7-bromo-9H-fluorene-2-carbaldehyde, m.p. 177-180° C. The yield is 57 or 63% based on assumed purity of 100% or 90% for the sample of 2-bromofluorene used. Mass spec: m/z 272, 274 (M$^+$). Anal Calcd for $C_{14}H_9BrO$: C, 61.57%; H, 3.32%; Br, 29.26%. Found: C, 61.53%; H, 3.44%; Br, 29.22%. $^1$H NMR (CDCl$_3$), δ ppm: 3.94 (s, 2H), 7.53-7.56 (dd, 1H), 7.68-7.72 (m, 2H), 7.85-7.91 (m, 2H), 8.03 (s, 1H), and 10.04 (s, 1H). $^{13}$C NMR: 36.57 (1 sp$^3$C), 120.19, 122.23, 122.46, 125.82, 128.55, 129.81, 130.40, 135.32, 139.21, 143.28, 146.45, 146.72, and 191.90 (13 sp$^2$C).

Additional quantity of 7-bromo-aldehyde product (10 to 12% yield) can be obtained from the filtrates by column chromatography by separating an isomeric bromo-aldehyde (11-12% yield).

7-Bromo-fluorene-4-carboxaldehyde m.p. 135-137° C. Mass spec: m/z 272, 274 (M$^+$). Anal Calcd for $C_{14}H_9BrO$: C, 61.57%; H, 3.32%; Br, 29.26%. Found: C, 61.54%; H, 3.24%; Br, 29.33%. $^1$H NMR (CDCl$_3$), δ ppm: 3.91 (s, 2H), 7.26-7.88 (m, 5H), 8.59 (d, 1H), and 10.43 (s, 1H). $^{13}$C NMR: 36.96 (1 sp$^3$C), 122.29, 126.79, 127.38, 127.89, 130.26, 130.29, 132.36, 132.58, 139.36, 141.03, 144.95, 146.28, and 192.30 (13 sp$^2$C).

EXAMPLE 12

2,6-Bis(7-bromo-9H-fluorenyl)benzo[1,2-d:4,5-d']bisthiazole

A mixture of 7-bromofluorene-2-carbaldehyde (Example 11; 11.0 g, 40.3 mmol), 2,5-diaminobenzene-1,3-dithiol dihydrochloride (5.00 g, 20.4 mmol), DMSO (145 mL), and tri-n-butylamine (12.0 mL), was held at 165-170° C. for 5 hours, cooled, and filtered. The solids were washed with acetic acid, and then water. These were suspended in acetic acid (200 mL), kept at reflux for 2 hours, cooled, and filtered to give 11.14 g (82% yield). Mass spec: m/z 676, 678, 680 (M$^+$). Anal. Calcd for $C_{34}H_{18}Br_2N_2S_2$: C, 60.19%; H, 2.67%; N, 4.13%; S, 9.45%; Br, 23.55%. Found: C, 60.04%, H, 2.89%; N, 4.18%; S, 9.76%; Br, 23.48%.

EXAMPLE 13

2,6-Bis[7-bromo-9,9-bis(3,7-dimethyloctyl-2-fluorenyl)]benzo[1,2-d:4,5-d']bisthiazole To a mixture of 2,6-bis(7-bromofluorenyl)benzobisthiazole (Example 12; 1.6 g, 2.36 mmol), 1-bromo-3,7-dimethyloctane (Example 1, 2.25 g, 9.3 mmol) and THF (55 mL), potassium t-butoxide (1.94 g, 17.3 mmol) was added and the mixture was stirred under nitrogen for 18 hours. Extractive work-up with toluene gave a product mixture which was chromatographed over silica gel. Elution with toluene-heptane (2:1) gave the product that solidified on standing with isopropanol, 1.13 g (39% yield), m.p. 151-153° C. Mass spec: m/z 1236, 1238, and 1240 (M$^+$). Anal. Calcd. for $C_{74}H_{98}N_2S_2Br_2$: C, 71.70%; H, 7.97%; N, 2.26%; S, 5.17%; Br 12.89%. Found: C, 71.60%; H, 8.11%; N, 2.29%; S, 5.34%; Br, 13.03%. $^1$H NMR (CDCl$_3$), δ ppm: 0.50-0.70 (m, 8H), 0.71-0.72 (m, 12H), 0.75-0.77 (m, 24H), 0.78-0.79 (m, 4H), 0.88-1.17 (m, 24H), 1.38-1.60 (m, 4H), 2.05-2.08 (m, 8H), 7.49-7.51 (m, 4H), 7.60-7.62 (m, 2H), 7.76-7.78 (m, 2H), 8.08-8.10 (m, 4H), and 8.57 (5, 2H). $^{13}$C NMR (CDCl$_3$), δ ppm: 19.44, 19.50, 22.50, 22.53, 22.61, 24.52, 24.54, 27.87, 27.90, 30.40, 30.46, 32.79, 36.50, 36.55, 37.45, 39.15, 55.60 (17 sp$^3$C), 115.13, 120.28, 121.66, 121.73, 122.21, 126.28, 127.22, 130.28, 132.64, 134.44, 139.16, 143.37, 151.23, 152.30, 153.60, and 169.23 (16 sp$^2$C).

EXAMPLE 14

2,6-Bis[7-bromo-9,9-bis(3,7,1'-trimethyldodecyl-2-fluorenyl)]benzo[1,2-d:4,5-d']bisthiazole In a similar manner as described in Example 13, 2,6-bis(7-bromofluorenyl)benzobisthiazole (Example 12; 1.4 g, 2.06 mmol) was alkylated with hexahydrofarnesyl bromide (Example 3) (3.0 g, 10.3 mmol) and potassium t-butoxide (2.2 g, 19.6 mmol). The desired product, 1.25 g (40% yield), was obtained after column chromatography. Mass spec: m/z 1517, 1519, and 1521 (M$^+$). Anal. Calcd. for $C_{94}H_{138}N_2S_2Br_2$: C, 74.27%; H, 9.15%; N, 1.84%; S, 4.22%; Br, 10.51%. Found: C, 74.06%; H, 9.04%; N, 1.84%; S, 4.24%; Br, 10.63%. $^1$H NMR (CDCl$_3$), δ ppm: 0.69 (m, 4H), 0.70 (m, 4H), 0.72-0.76 (m, 24H), 0.81-0.85 (m, 4H), 2.07 (m, 8H), 7.48-7.53 (m, 4H), 7.60-7.65 (m, 2H), 7.79 (d, 2H), 8.08-8.14 (m, 4H), 8.58 (s, 2H). $^{13}$C NMR (CDCl$_3$), δ ppm: 19.38, 19.46, 19.53, 19.61, 19.63, 22.58, 22.60, 22.68, 24.24, 24.72, 24.75, 27.92, 27.93, 30.37, 30.49, 30.55, 32.68, 32.70, 32.75, 32.80, 36.57, 36.61, 36.65, 37.22, 37.24, 37.30, 37.46, 39.30, 55.59 (29 sp$^3$C), 115.14, 120.28, 121.66, 122.21, 126.27, 127.21, 130.27, 132.61, 134.42, 139.15, 143.38, 151.22, 152.28, 153.58, and 169.23 (15 sp$^2$C).

EXAMPLE 15

2,6-Bis[7-bromo-9,9-bis(3,7,11,15-tetramethylhexadecylfluoren-2-yl)]benzo[1,2-d:4,5-d']bisthiazole Following the procedure described in Example 13, 2,6-Bis (7-bromofluorenyl)benzobisthiazole (Example 12; 6.12 g, 9.02 mmol) was similarly alkylated with dihydrophytyl bromide (Example 5; 15.52 g, 42.9 mmol) and potassium t-butoxide (8.31 g, 74.0 mmol) in THF (250 mL). The desired product, 6.84 g (42% yield), was obtained after chromatographic purification on a silica gel column, and elution with 15% toluene-heptane. Mass spec: m/z 1797, 1799, and 1801 (M$^+$). Anal. Calcd. for $C_{114}H_{178}Br_2N_2S_2$: C, 76.04%; H, 9.96%; N, 1.56%; S, 3.56%; Br, 8.88%. Found: C, 74.26%; H, 9.54%; N, 1.42%; S, 3.32%; Br, 9.50%. Without further purification, this material was used in the next step of the synthesis to produce AF-388-416 (Example 23).

EXAMPLE 16

2-(4-Diphenylaminophenyl)-4,4,5,5-tetramethyl-1,3,2-dioxaborolane

To a flame-dried 3-neck, round-bottomed 500 mL flask equipped with mechanical stirring and an addition funnel was added 4-bromotriphenylamine (12.5 g, 39.5 mmol) and THF (250 mL) by cannula. The solution was cooled to −78° C. and 1.6 M n-BuLi in hexane (26.5 mL, 42.4 mmol) was added by addition funnel over 15 min. After stirring for 30 min, 2-isopropoxy-4,4,5,5-tetramethyl-1,3,2-dioxaborolane (9.8 mL, 48.2 mmol) was added dropwise, and the reaction mixture was allowed to warm to room temperature overnight. Toluene and water were added, and the organic phase was further washed with water, dried with $MgSO_4$, and concentrated. The crude product was purified by column chromatography eluting with hexane, 2/1 hexane/$CH_2Cl_2$, and finally 1/1 hexane/$CH_2Cl_2$ to give 6.4 g (45%) white crystals. $^1$H NMR (400 MHz, $CDCl_3$) δ: 7.66 (m, 2H), 7.26 (m, 4H), 7.10 (m, 4H), 7.04 (m, 4H); GC-MS (m/z): 371 (M$^+$), >97% purity. Anal. Calcd. for $C_{24}H_{26}BNO_2$: C, 77.64%; H, 7.06%; B, 2.91%; N, 3.77%. Found: C, 77.78%; H, 7.21%; B, 2.70%; N, 3.53%.

EXAMPLE 17

2,6-Bis{4-diphenylaminophenyl-7-[9,9-bis(3,7-dimethyloctyl)]fluoren-2-yl}-benzo[1,2-d;4,5-d']bisthiazole (AF-358-118)

A mixture 2,6-bis[7-bromo-9,9-di(3,7,11-trimethyldodecyl-2-fluorenyl)]benzo[1,2-d:4,5-d']bisthiazole (Example 14; 0.99 g, 2.66 mmol), 2-(4-diphenylaminophenyl)-4,4,5,5-tetramethyl-1,3,2-dioxaborolane (Example 16, 1.5 g, 1.21 mmol), toluene (30 mL), 2M $Na_2CO_3$ (6 mL), and a few drops of Aliquat 336 was degassed by argon bubbling for 20 min. Pd(PPh$_3$)$_4$ (42 mg, 0.036 mmol) was then added, and the mixture was placed in a thermostated oil bath at 90° C. for 48 hr. Upon cooling to room temperature, the solution was diluted with toluene and washed with water and brine. Purification by column chromatography eluting with 50/50 toluene/heptanes gave 1.43 g (75%) which was crystallized from heptane/ethanol. $^1$H NMR (400 MHz, $CDCl_3$) δ 8.57 (s, 2H), 8.10 (m, 4H), 7.80 (t, J=7.9 Hz, 4H), 7.57 (m, 8H), 7.30-7.15 (m, 20H), 7.05 (t, J=7.3 Hz, 4H) 2.13 (m, 8H), 1.37 (m, 4H), 1.20-0.50 (br, 72H); $^{13}$C NMR (100 MHz, $CDCl_3$) δ 169.52, 152.29, 152.14, 151.79, 147.63, 147.28, 144.34, 140.56, 139.01, 135.26, 134.41, 132.07, 129.31, 127.84, 127.16, 125.81, 124.45, 123.86, 123.01, 121.69, 120.92, 120.64, 120.15, 115.02, 55.35, 39.19, 37.62, 36.67, 36.50, 32.86, 30.57, 30.49, 27.91, 27.88, 24.60, 22.64, 22.53, 19.61, 19.49; EI-MS (m/z): 1571 (M$^+$), 784 (M$^{++}$); Anal. Calcd. for $C_{110}H_{126}N_4S_2$: C, 84.24%; H, 8.10%; N, 3.57%; S, 4.09%. Found: C, 83.95%; H, 8.06%; N, 3.75%; S, 3.98%.

EXAMPLE 18

7-Bromo-9,9-bis(3,7,11-trimethyldodecyl)fluorene-2-carbaldehyde 2,7-Dibromo-9,9-bis(3,7,11-trimethyldodecyl)fluorene (Example 7; 21.02 g, 28.25 mmol) was reacted with n-butyllithium (1.6 M, 16.5 mL, 26.4 mmol) in THF at −78° C., and quenched with N-formyl piperidine (4.7 mL, 42.3 mmol). The crude product was chromatographed over silica gel eluting with 15 and 25% toluene-heptane to get the aldehyde product as a liquid, 13.11 g (72% Yield). Mass spec: m/z 692, 694 (M$^+$). Anal Calcd for $C_{44}H_{69}BrO$: C, 76.16%; H, 10.02%; Br 11.51%. Found: C, 76.39%; H, 9.85%; Br, 11.49%. $^1$H NMR ($CDCl_3$), δ ppm: 0.51-0.54 (m 4H), 0.67 (tt, 6H), 0.77 (tt, 6H), 0.85 (d, 12H), 0.92-1.26 (m, 30H), 1.47-1.53 (m, 2H), 1.98-2.02 (m 4H), 7.50-7.65 (m, 3H), 7.79-7.87 (m, 3H), 10.05 (s, 1H).

EXAMPLE 19

7-Bromo-9,9-bis(3,7,11,15-tetramethylhexadecyl)fluorene-2-carbaldehyde

Method A 2.7-Dibromo-9,9-bis(dihydrophytyl)fluorene (Example 8; 29.0 g, 32.76 mmol) was reacted with n-butyllithium (2.5 M, 12.5 mL, 31.25 mmol) and quenched with formyl piperidine (6 mL, 54 mmol). After chromatographic purification the aldehyde product was obtained as a liquid, 22.03 g (84% Yield). Mass spec: m/z 832, 834 (M$^+$). Anal Calcd for $C_{54}H_{89}BrO$: C, 77.75%; H, 10.75%; Br, 9.58%. Found: C, 78.47%; H, 10.68%; Br, 9.30%.

Method B 2-(7-Bromofluoren-2-yl)-1,3-dioxolane

A mixture of 7-bromofluorene-2-carboxaldehyde (Example 11; 14.0 g), ethylene glycol (10.0 mL), toluene (200 mL), and p-toluenesulfonic acid monohydrate (1.2 g) was kept at reflux for 2 hours, and cooled in an ice bath. A dilute solution of sodium bicarbonate was added, and the mixture was diluted with heptane. The separated solids were collected by filtration and washed with 1:1 toluene-heptane to get the product, 13.98 g (84% yield), m.p. 156-159° C. Mass spec: m/z 316, 318 (M$^+$).

(ii) Alkylation of 2-(7-bromofluoren-2-yl)-1,3-dioxolane with dihydrophytyl bromide 2-(7-Bromo-9,9-bis(3,7,11,15-tetramethylhexadecylfluoren-2-yl)-1,3-dioxolane: To a mixture of 2-(7-bromofluoren-2-yl)-1,3-dioxolane (4.85 g, 15.0 mmol), 3,7,11,15-tetramethylhexadecyl bromide (Example 5) (12.65 g, 35 mmol), and THF (250 mL) cooled to 5° C. under nitrogen was added potassium-t-butoxide (6.19 g, 55.0 mmol) in two portions over a 30-minute interval. The mixture was allowed to come to room temperature and was stirred at room temperature for 20 hours. To the resulting greenish gray mixture, sodium bicarbonate (6.0 g) was added followed by water and toluene. The organic phase was dried and then concentrated. Column chromatography of the residue over alumina gave the product contaminated with unreacted alkyl bromide. This product was stirred with pyridine (5.0 mL) for 2 days and worked up by extraction into toluene. The toluene extract was chromatographed over alumina, and the column was eluted with heptane and 5% toluene-heptane to afford the desired product, 7.81 g (58% yield). Mass spec: m/z 876, 878 (M$^+$). Anal. Calcd for $C_{56}H_{93}BrO_2$: C, 76.59%; H, 10.67%; Br, 9.10%. Found: C, 76.50%; H, 10.81%; Br, 9.55%.

(iii) 7-Bromo-9,9-bis(3,7,11,15-tetramethylhexadecylfluorene-2-carbaldehyde

A mixture of the dialkylated acetal (7.4 g) from the step (ii), toluene (5 mL), acetic acid (25 mL), hydrochloric acid (5 mL), and water (25 mL) was kept under reflux for 3 hours, and worked up by extraction into toluene. The crude product was chromatographed over silica gel. Elution with 15% toluene-heptane gave the product as a colorless liquid, 6.97 g (99% yield). Mass spec: m/z 832, 834 (M$^+$). Anal. Calcd for $C_{54}H_{89}BrO$: C, 77.75%; H, 10.75%; Br, 9.58%. Found: C, 77.50%; H, 10.36%; Br, 9.71%. $^1$H NMR (CDCl$_3$), δ ppm: 0.52-0.55 (m, 2H), 0.66-0.69 (m, 6H), 0.75-0.78 (M, 6H), 0.82-0.90 (m 24H), 0.93-1.36 (m, 38H), 1.48-1.55 (m, 2H), 1.98-2.02 (m, 4H), 7.49-7.52 (m, 2H), 7.62-7.65 (m, 1H), 7.80-7.87 (m, 3H). $^{13}$C NMR (CDCl$_3$), δ ppm: 19.52, 19.59, 19.70, 19.83, 19.90, 22.78, 22.88, 24.36, 24.45, 24.60, 24.95, 28.12, 30.54, 30.67, 32.03, 32.92, 36.79, 37.33, 37.42, 37.53, 37.58, 39.50, 55.59 (23sp$^3$C), 120.25, 122.39, 123.27, 125.44, 126.54, 128.37, 129.18, 129.82, 130.60, 135.76, 138.77, 146.56, 151.23, 154.35, and 192.33 (15 sp$^2$ C).

EXAMPLE 20

2,6-Bis[7-bromo-9,9-bis(3,7,11,15-tetramethylhexdecyl)-fluoren-2-yl]-benzobisthiazole A mixture of 7-bromo-9,9-bis(3,7,11,15-tetramethylhexadecyl)-fluorene-2-carbaldehyde (Example 19) (6.8 g, 8.15 mmol), 2,5-diaminobenzene-1,4-dithiol dihydrochloride (0.99 g, 4.07 mmol), tri-n-butylamine (2.8 mL, 11.7 mmol) toluene (10 mL) and DMSO (10 mL) was heated to 150° C. allowing toluene to distill off and was held at this temperature for 3 hours. After cooling, the mixture was diluted with ethyl acetate, and the solution was washed with water, dried, and concentrated. The residue was chromatographed over silica gel. Elution of the column with a mixture of heptane and toluene (3:1), gave the liquid product, 3.68 g (50% Yield). Mass spec: m/z 1798.8, 1799.9, 1800.9, 1801.9, and 1802.8 (M$^+$, MALDI). Anal Calcd for $C_{114}H_{178}Br_2N_2S_2$: C, 76.04%; H, 9.96%; N, 1.56%; S, 3.56%; Br, 8.88%. Found: C, 76.10%; H, 9.92%; N, 1.50%; S, 3.43%; Br, 8.86%. $^1$H NMR (CDCl$_3$), δ ppm: 0.69-1.55 (m, 156H), 1.88-2.20 (m, 8H), 7.49-7.80 (m, 8H), 8.09-8.11 (m, 4H), and 8.57 (s, 2H). $^{13}$C NMR, (CDCl$_3$), δ ppm: 19.53, 19.62, 19.70, 19.77, 19.83, 19.88, 19.90, 22.79, 22.89, 24.43, 24.60, 24.95, 28.12, 30.56, 32.89, 32.91, 32.93, 32.98, 36.76, 36.84, 37.37, 37.42, 37.52, 37.56, 39.51, 55.76 (26 sp$^3$C), 115.31, 120.46, 121.84, 122.38, 126.43, 127.39, 130.44, 132.78, 134.59, 139.32, 143.55, 151.39, 152.45, 153.75, and 169.41 (15 sp$^2$C).

EXAMPLE 21

2,6-Bis[7-(diphenylimino)-9,9-bis(3,7-dimethyloctyl)]fluoren-2-yl)]-benzobisthiazole (AF-388-118)

A mixture of 2,6-[bis(7-bromo-9,9-bis(3,7-dimethyloctyl) fluoren-2-yl)]-benzobisthiazole (Example 10) (6.18 g, 4.99 mmol), diphenylamine (2.5 g, 14.8 mmol) and toluene (100 mL) was azeotropically dried under nitrogen and cooled. Bis-(dibenzylideneacetone)palladium(0) (85.5 mg, 0.15 mmol), 1,1'-bisdiphenylphosphino-ferrocene (86.3 mg, 0.16 mmol), and sodium t-butoxide (2.35 g, 24.45 mmol) were added, and the mixture was held at 105° C. for 2 hours. After cooling, the mixture was diluted with toluene and water, the toluene phase was washed with water, dried and concentrated. The residue was chromatographed over silica gel, and the column was eluted with toluene-heptane (1:1) to get the product. The crude product was crystallized from a mixture of toluene and ethanol, 5.68 g (81% Yield), m.p. 171-172° C. A 0.24 M solution in toluene remained homogenous, where as a 0.34 M solution solidified at room temperature after 72 hours. Mass spec: m/z 1416 (M+). Anal Calcd for $C_{98}H_{118}N_4S_2$: C, 83.12; H, 8.40; N, 3.96; S, 4.53%. Found: C, 83.07; H, 8.43; N, 4.05; S, 4.47%. $^1$H NMR (CDCl$_3$) δ ppm: 0.70-0.77 (m, 4H), 0.78 (d, 12H), 0.78 (m, 4H), 0.80 (d, 24H), 1.02-1.03 (m, 4H), 1.03-1.13 (m, 24H), 1.13-1.15 (m, 4H), 1.41-1.63 (m, 8H), 7.02-7.06 (m, 6H), 7.13-7.15 (m, 10H), 7.25-7.28 (m, 8H), 7.61 (d, 2H), 7.70 (d, 2H), 8.05-8.07 (m, 4H), 8.54 (s, 2H). $^{13}$C NMR, (CDCl$_3$) δ ppm: 19.46, 19.73, 22.53, 22.56, 22.65, 22.66, 24.80, 24.57, 27.66, 27.84, 27.89, 28.00, 30.55, 30.83, 32.87, 32.89, 36.63, 36.90, 37.35, 37.67, 39.14, 39.21, 55.19 (23 sp$^3$C), 114.88, 118.60, 118.65, 119.46, 121.08, 121.46, 122.79, 123.21, 123.28, 123.77, 124.09, 124.11, 127.17, 128.94, 129.23, 131.37, 131.38, 134.31, 134.99, 135.01, 144.39, 147.77, 148.10, 151.37, 152.22, 152.86, 169.51, and 169.53 (28 sp$^2$C).

EXAMPLE 22

2,6-Bis[7-(diphenylimino)-9,9-bis(3,7,1'-trimethyl-dodecylfluoren-2-yl)]-benzobisthiazole (AF-388-312)

Using a similar procedure as in Example 20, hexahydro-farnesyl-substituted bromofluorenyl benzobisthiazole (Example 14; 4.92 g, 3.24 mmol) was aminated using diphenylamine (1.65 g, 9.8 mmol), bis(dibenzylideneacetone) palladium(0) (61.2 mg, 0.11 mmol), 1,1'-bisdiphenylphosphino-ferrocene (59.6 mg, 0.11 mmol), and sodium t-butoxide (1.64 g, 17 mmol) in toluene (62 mL) at 80° C. for 17 hours. Column chromatography over silica gel and elution with toluene-heptane (3:5) gave the product, which was crystallized from a mixture of isopropanol and hexanes, 4.43 g (81%), m.p. 107-108.5° C. A 0.34 M solution in toluene remained homogenous for months. Mass spec: m/z 1696 (M$^+$). Anal Calcd for $C_{118}H_{158}N_4S_2$: C, 83.53%; H, 9.39%; N, 3.30%; S, 3.78%. Found: C, 83.37; H, 9.44; N, 3.42; S, 3.87%. $^1$H NMR (CDCl$_3$), δ ppm: 0.48-0.58 (m, 4H), 0.65-0.77 (m, 28H), 0.81-0.84 (m, 24H), 0.88-1.22 (m, 56H), 1.42-1.51 (m, 4H), 1.90-2.07 (m, 8H), 7.02-7.06 (m, 6H), 7.13-7.15 (m, 10H), 7.25-7.28 (m, 8H), 7.62 (d, 2H), 7.71 (d, 2H), 8.06-8.08 (m, 4H), and 8.55 (s, 2H). $^{13}$C NMR (CDCl$_3$), δ ppm: 19.44, 19.53, 19.60, 19.67, 19.70, 19.73, 19.79, 22.65, 22.73, 24.34, 24.57, 24.76, 24.79, 27.97, 27.98, 30.62, 30.72, 30.86, 31.02, 32.71, 32.73, 32.79, 32.97, 36.77, 36.83, 37.08, 37.28, 37.30, 37.33, 37.38, 37.40, 37.73, 39.34, 39.36, 55.24 (35 sp$^3$C), 114.94, 118.68, 118.74, 119.50, 121.12, 121.52, 122.82, 123.35, 124.13, 127.21, 129.28, 131.44, 134.36, 135.07, 144.44, 147.83, 148.14, 151.43, 152.28, 152.91, and 169.55 (21 sp$^2$C).

EXAMPLE 23

2,6-Bis[7-(diphenylimino)-9,9-bis(3,7,11,15-tetramethylhexadecyl)fluoren-2-yl]-benzobisthiazole (AF388-416)

Similar amination of dihydrophytyl-substituted bromofluorenyl benzobisthiazole (see Example 20; 6.84 g, 3.8 mmol) with diphenylamine (1.65 g, 9.8 mmol), bis(dibenzylideneacetone)palladium(0) (75.6 mg, 0.13 mmol), 1,1'-bisdiphenylphosphino-ferrocene (71.8 mg, 0.13 mmol) and sodium t-butoxide (2.03 g) in toluene (2.03 g, 21.0 mmol), after a 4 hour reaction at 94° C. and column chromatography over silica gel gave the product that resisted various attempts to get it as a solid, 4.47 g (59% Yield). Mass spec: m/z 1977 (M$^+$). Anal Calcd for $C_{138}H_{198}N_4S_2$: C, 83.82%; H, 10.10%; N, 2.83%; S, 3.24%. Found: C, 83.88%; H, 10.03%; N, 2.85%; S, 3.22%. $^1$H NMR (CDCl$_3$), δ ppm: 0.42-0.60 (m, 4H), 0.69-0.83 (m, 68H), 0.84-1.40 (m, 80H), 1.42-1.58 (m, 4H), 1.82-2.2 (m, 8H), 7.02-7.06 (m, 6H), 7.12-7.15 (m, 10H), 7.25-7.28 (m, 8H), 7.62 (d, 2H), 7.71 (d, 2H), 8.06-8.08 (m, 4H), and 8.55 (s, 2H). $^{13}$C NMR, (CDCl$_3$), δ ppm: 19.38, 19.48, 19.54, 19.55, 19.62, 19.66, 19.68, 19.71, 22.63, 22.72, 24.33, 24.40, 24.43, 24.54, 24.79, 27.95, 30.61, 30.70, 30.83, 31.00, 32.69, 32.73, 32.75, 32.77, 32.91, 32.95, 36.76, 36.82, 37.07, 37.25, 37.26, 37.30, 37.34, 37.36, 37.41, 37.45, 37.50, 37.69, 39.34, 55.20 (40 sp$^3$C), 114.91, 118.70, 119.46, 121.08, 121.48, 122.79, 123.24, 123.30, 124.09, 127.17, 129.24, 131.40, 134.32, 135.04, 144.40, 147.79, 148.10, 151.39, 152.24, 152.87, and 169.50 (21 sp$^2$C).

EXAMPLE 24

Comparison of Solubility of Diphenylaminodialkylfluorene-Benzobisthiazole-Diphenylaminodialkylfluorene Chromophores (AF388 Series)

To illustrate the drastic effect of having multi-branched alkyl chains on the solubility in hydrocarbon solvents, the solubilities in hexane and toluene at room temperature for the AF-388 series were determined and compared. From the data (solubility in hexane at 24° C.) in the following table, It is obvious that branched alkyl groups increase hydrocarbon solubility (as an indicator for oleophilicity) when comparing alkyl chains with the same formula (i.e. $C_{10}H_{21}$ for linear and di-branched alkyl chain), and the change is even more dramatic when both length and branching frequency of the alkyl chains are increased at the same time.

In addition, these chromophores are found to be even more soluble in aromatic hydrocarbon solvents as indicated by the higher solubilities of AF388-118 ($\geqq$29 wt %) and AF388-312 ($\geqq$67 wt %) in toluene.

|  | Linear or branched alkyl chain (R) | % wt/wt | % wt/vol. |
|---|---|---|---|
| AF-388 | (—$C_{10}H_{21}$; n-decyl) | 0.01 | 0.008 |
| AF-388-118 | (—$C_{10}H_{21}$; 3,7-dimethyloctyl) | 0.61 | 0.41 |
| AF-388-312 | (—$C_{15}H_{31}$; 3,7,11-trimethyldodecyl) | 30.4 | 20.2 |
| AF-388-416 | (—$C_{20}H_{41}$; 3,7,11,15-tetramethylhexadecyl) | 51.3 | 36.3 |

EXAMPLE 25

Two-Photon Properties of AFX Chromophore Solutions

The two-photon activity at 800 nm of AF358-118 (Example 16 in THF solution (0.02 M) was confirmed under femtosecond-pulsed laser excitation by a standard open-aperture Z-scan experiment, and the intrinsic 2PA cross-section ($\sigma_2'$) was determined. Thus, $\sigma_2'$ value in solution was 84±4 GM (1GM=$10^{-50}$ cm$^4$·sec/photon). In addition, femtosecond two-photon-induced fluorescence (TPIF) method was also used to generate the two-photon spectrum (~600 nm to 900 nm) for AF358-118 in THF solution ($10^{-5}$ M). It was found that the peak $\sigma_2'$ value was 1,520 GM at ~760 nm and the 800 nm value was ~800 GM.

For the AF-388 series, the effective 2PA cross-sections are expected to be in the same range as that of AF-388 (with n-octyl groups), i.e. 23,400 GM at 800 nm (±15% uncertainty), which was obtained by a nonlinear transmission technique using a 8 ns laser and a 0.02 M THF solution sample.

Having thus described exemplary embodiments of the present invention, it should be noted by those skilled in the art that the disclosures herein are exemplary only and that alternatives, adaptations and modifications may be made within the scope of the present invention.

We claim:
1. A chromophore of the formula:

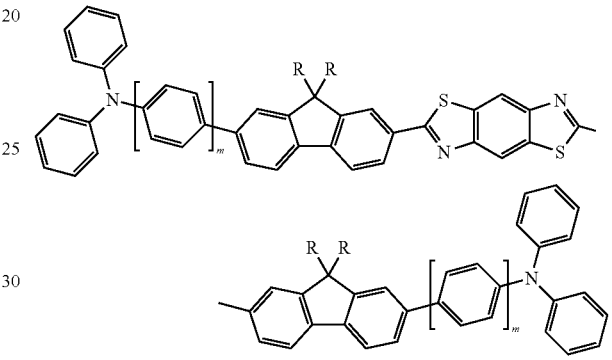

wherein m=0, 1 or 2; and wherein R is a multi branched alkyl chain having the formula $C_nH_{2n+1}$, where n=10-20.

2. The chromophore of claim 1 wherein R is selected from the group consisting of 3,7-dimethyloctyl, 3,7,11-trimethyldodecyl, 3,7,11,15-tetramethylhexadecyl, and mixtures thereof.

3. The chromophore of claim 2 wherein R is 3,7-dimethyloctyl.

4. The chromophore of claim 2 wherein R is 3,7,11-trimethyldodecyl.

5. The chromophore of claim 2 wherein R is 3,7,11,15-tetramethylhexadecyl.

6. The chromophore of claim 1 wherein m=1.
7. The chromophore of claim 2 wherein m=1.
8. The chromophore of claim 2 wherein m=1.
9. The chromophore of claim 2 wherein m=1.
10. The chromophore of claim 1 wherein m=1.
11. The chromophore of the formula:

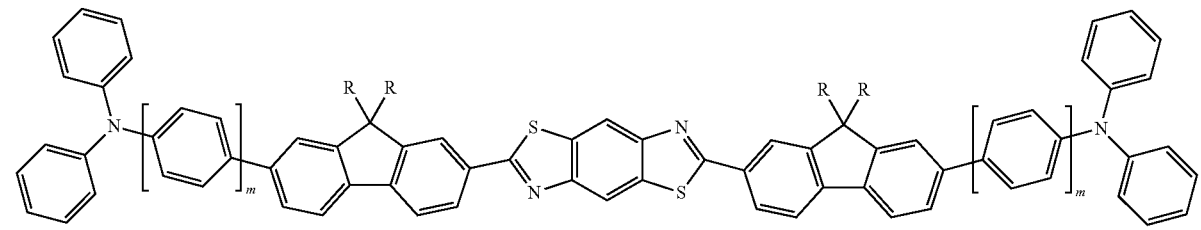

wherein m=1, or 2; and R is an alkyl chain having the formula $C_nH_{2n+1}$, wherein n=10-20.

* * * * *